United States Patent [19]

Takahashi

[11] Patent Number: 4,671,630
[45] Date of Patent: Jun. 9, 1987

[54] ILLUMINATING OPTICAL SYSTEM FOR ENDOSCOPES

[75] Inventor: Susumu Takahashi, Hachiouji, Japan

[73] Assignee: Olympus Optical Co., Ltd., Tokyo, Japan

[21] Appl. No.: 820,304

[22] Filed: Jan. 21, 1986

Related U.S. Application Data

[62] Division of Ser. No. 646,221, Aug. 31, 1984, abandoned, which is a division of Ser. No. 381,885, May 25, 1982, Pat. No. 4,500,181.

[30] Foreign Application Priority Data

May 26, 1981 [JP]  Japan ................................. 56-79921

[51] Int. Cl.$^4$ ........................ G02B 5/04; G02B 23/02; A61B 1/06
[52] U.S. Cl. .................................. 350/574; 350/527; 350/96.26; 350/286; 362/32; 128/6
[58] Field of Search ............... 350/573, 523, 527, 506, 350/96.26, 286, 287, 574; 362/32; 128/6

[56] References Cited

U.S. PATENT DOCUMENTS 3,261,349  7/1966  Wallace ............................. 350/96.26
3,548,808  12/1970  Takahashi ......................... 350/96.26
3,643,653  2/1972  Takahashi et al. .................... 128/6

FOREIGN PATENT DOCUMENTS 55-60432  5/1980  Japan .

Primary Examiner—Jon W. Henry
Attorney, Agent, or Firm—Cushman, Darby & Cushman

[57] ABSTRACT

An illuminating optical system for endoscopes comprising a prism having surfaces adapted to totally reflect the light led into the prism and a surface adapted to project the light toward an object to be observed, and at least one tubular transparent member adjacent on one end face to a light source and contacting on the other end face with one of the surfaces of the prism to lead the light from the light source into the prism, so that, in spite of a high magnification, the uniform illumination is made and a clear stereoscopic image having no flare is always obtained. This prism may be arranged coaxially to or in parallel with the observing optical system. The tubular transparent member has an outer peripheral surface provided thereon a light shielding member and an inner peripheral surface which can scramble-reflect the light introduced into the interior.

26 Claims, 18 Drawing Figures

ILLUMINATING OPTICAL SYSTEM FOR ENDOSCOPES

This is a division of application Ser. No. 646,221, filed Aug, 31, 1984, now abandoned which was a division of Ser. No. 381,885 filed May 25, 1982, now U.S. Pat. No. 4,500,181.

BACKGROUND OF THE INVENTION (a) Field of the Invention

This invention relates to an illuminating optical system adapted to endoscopes particularly of a high magnification.

(b) Description of the Prior Art

Figure 1:
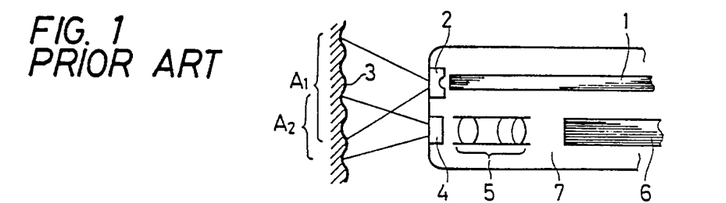
FIG. 1 is an explanatory view showing the formation of a tip part of a conventional high magnification endoscope.

In order to well observe the structure within a human body, it is necessary to use an endoscope high in the magnification. Therefore, hitherto it has been usual to use an endoscope of a type provided with an illuminating optical system on the side of an observing optical system as set very close to an object to be observed as shown in FIG. 1. That is to say, in FIG. 1, the reference symbol $A_1$ shows a range to be illuminated on a surface 3 of an object to be observed of an illuminating light projected out of light guide fibers 1 through an illuminating optical system 2 and $A_2$ shows a range to be observed on the surface 3 of the object to be observed of an observing optical system including a cover glass 4, objective 5 and image guide 6. In such formation, there have been defects that, in case the surface 3 of the object to be observed and the tip part 7 of the endoscope are made to approach to each other, the range $A_1$ to be illuminated and range $A_2$ to be observed will not coincide with each other and the uneven illumination will be made due to a parallax. There have been also defects that, in case the magnification of the observing optical system is high, the focal depth will be so shallow that, if the distance between the surface 3 of the object to be observed and the tip surface of the endoscope varies, the image will be likely to be out of focus and, if the tip part 7 of the endoscope deviates, in the case of photographing, the image will be likely to be fluid.

Figure 2:
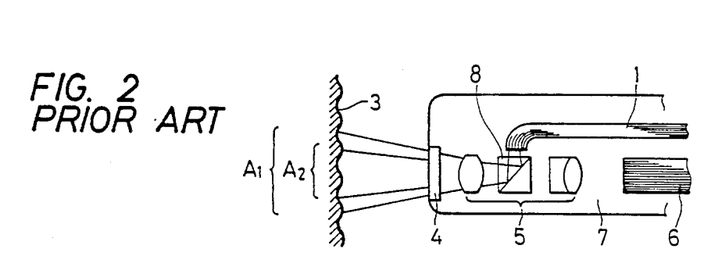
FIG. 2 is an explanatory view showing the formation of a tip part of a conventional high magnification endoscope designed to eliminate the unevenness of the illumination.
Figure 3:
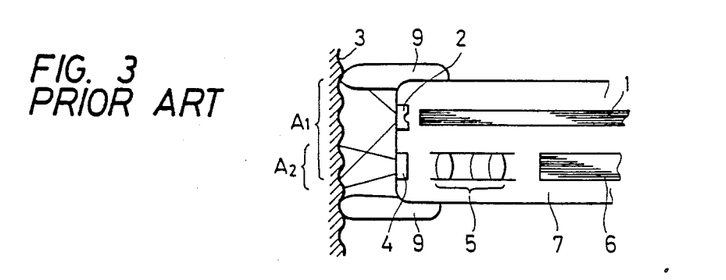
FIG. 3 is an explanatory view of the case that a hood is fitted to a tip part of a conventional high magnification endoscope.
Figure 4:
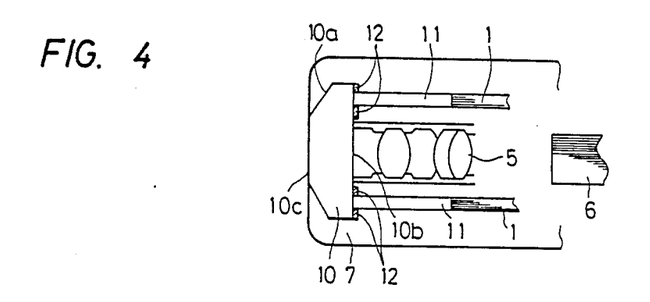
FIG. 4 is an explanatory view showing the formation of a tip part of a high magnification endoscope containing an embodiment of the illuminating optical system according to the present invention.
Figure 5:
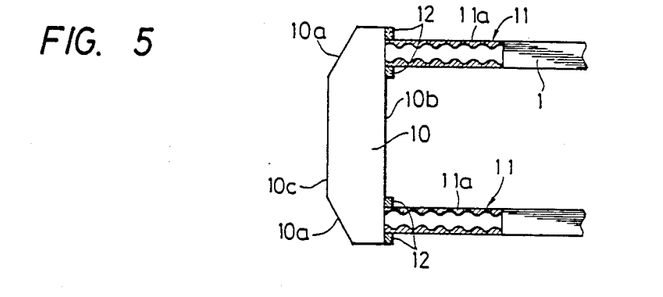
FIGS. 5 to 11 are explanatory views for explaining the operation of the embodiment shown in FIG. 4.
Figure 6:
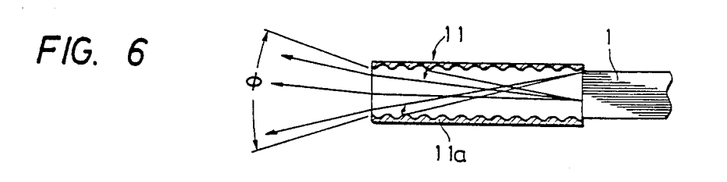

In order to eliminate such defects, such improvements as are shown in FIGS. 2 and 3 have been already made. First shown in FIG. 2 is a structure in which an illuminating optical system and observing optical system are coaxially arranged so as to eliminate the unevenness of the illumination caused by the non-coincidence of the ranges $A_1$ and $A_2$ with each other. A half-prism 8 is inserted in the objective 5 so that the light bundle projected out of the light guide fibers 1 will enter the side surface of the half-prism 8, will then be reflected and will be projected toward the surface 3 of the object to be observed out of the cover glass 4 of the observing optical system. Therefore, in this case, even if the tip part 7 of the endoscope approaches the surface 3 of the object to be observed, the illuminated range $A_1$ will be able to well cover the observed range $A_2$. However, in this system, there is a defect that no clear image can be obtained due to such flare as of the surface of the cover glass 4. Next shown in FIG. 3 is a method wherein at least a pair of projections 9, 9 opposed to each other are provided in the tip part of the endoscope to keep constant the distance between the surface 3 of the object to be observed and the tip surface of the endoscope so that, at the time of the observation, these projections 9 will be in close contact with the surface 3 of the object to be observed. However, even in this method, in case the magnification of the objective 5 is more than twice as large, the focal depth will become so shallow that, if the distance to the surface of the object to be observed varies, the image will be likely to be out of focus. It has been inconvenient.

SUMMARY OF THE INVENTION

A primary object of the present invention is to provide an illuminating optical system for endoscopes wherein, in view of the above mentioned circumstances, in spite of a high magnification, the uneven illumination will not be made and a clear stereoscopic image having no flare can be always obtained.

According to the present invention, this object is attained by a system wherein, when the refractive index of a transparent body to be arranged in front of an illuminating light source is represented by $n_2$ and the refractive index of a medium located on the side near to the light source from the transparent body is represented by $n_3$, the condition that $n_2 > n_3$ will be satisfied and the shape of the transparent body is so selected that the entrance agle of the light entering the surface of the transparent body directed to the light source side among lights entering the transparent body from the light source may be larger than a critical angle $$\theta_1 \left( \theta_1 = \sin^{-1} \frac{n_3}{n_2} \right)$$

at the entering point of the light.

According to a preferred formation of the present invention, the transparent body is a prism having a first surface facing the objective, a reflecting surface at an angle $\theta$ with the first surface and a second surface parallel with the first surface and is provided with tubular transparent members each adjacent on one end face to the light source and contacting on the other end face with the above mentioned first surface so as to lead the light from the light source toward the above mentioned reflecting surface.

This tubular transparent member has an outer peripheral surface provided thereon a light shielding member (a black coating) and an inner peripheral surface which can scramble-reflect the light introduced into the interior. A plurality of such tubular transparent members are arranged around the objective. This tubular transparent member may be a metal pipe having a threaded inner peripheral surface. Further, the first surface of the prism may be provided with a light shielding painted in member except in the effective diameter part of the objective and the connecting parts with the tubular transparent members so that the first surface may substantially serve as a reflecting face.

The angle $\theta$ made by the first surface and reflecting surface is so selected that the light reflected by this reflecting surface may be totally reflected by the first surface. Thereby, when the second surface is pressed against an object to be observed within a human body, by the cooperation with water enclosed between the second surface and the object, the light advancing through the prism will be effectively projected on the object side and the flare to enter the objective will be removed. The exit angle of the light coming out of the second surface will become so large that, as a result, the object surface will be diagonally illuminated and the image of the object to be observed will be able to be observed as a stereoscopic image.

According to another preferred formation of the present invention, the transparent body is a rectangular parallelepipedal prism having a first surface facing the objective, a second surface facing the object to be observed and parallel with the first surface and four side surfaces and is provided with tubular transparent members each adjacent on one end face to the light source and contacting on the other end face with the side surface to lead the light from the light source into the prism.

The tubular transparent member is formed in the same manner as described above. A plurality of such tubular transparent members are arranged around the objective. The first surface of this rectangular parallelepipedal prism may be provided with a light shielding member except in the effective diameter part of the objective and the side surfaces may also be provided with a light shielding member except in the connecting parts with the tubular transparent members, so that the first surface and side surfaces may substantially serve as reflecting faces.

The light from the light source may be led into the rectangular parallelepipedal prism through a triangular prism and the tubular transparent member connected to the triangular prism.

According to still another preferred formation of the present invention, the transparent body is a prism having a first surface facing the objective, a second surface facing the objective to be observed and parallel with the first surface and a third surface contacting at an angle with the first surface and is provided with tubular transparent members each adjacent on end face to the light source and contacting on the other end face with the third surface to lead the light from the light source into the prism. The first surface may form a predetermined angle with the second surface.

The angle between the first and third surfaces is so selected that, in case air is in contact with the second surface, the light led into the prism is totally reflected on the second surface.

This and other objects of the present invention will become more apparent during the course of the following detailed description and appended claims.

DESCRIPTION OF THE PREFERRED EMBODIMENTS

The present invention shall be explained by attaching the same reference numerals to substantially the same component parts and portions as are shown in FIGS. 1 to 3 on the basis of various embodiments illustrated in the following. First of all, in FIGS. 4 to 10, the reference numeral 10 denotes a prism serving as a transparent body set in front of the objective 5 within the tip part 7 of the endoscope and having a reflecting surface 10a, a surface (which shall be called an objective side surface hereinafter) 10b intersecting at right angles with the optical axis of the objective 5 and facing the objective 5 and a surface (which shall be called an object side surface hereinafter) 10c parallel with the objective side surface 10b and exposed to the front surface to the tip part 7 of the endoscope, 11 denotes a plurality of tubular transparent members each having an outer peripheral surface provided thereon a light shielding member (a black coating) 11a and not ground, one end face in close contact with or connected to the light guide fibers 1 and the other end face in close contact with or connected to the objective side surface 10b of the prism 10 and arranged around the objective 5 so as to lead the light from the light guide fibers 1 into the prism 10 and 12 denotes a light shielding member applied onto the objective side surface 10b except in the connecting faces with the transparent members and the effective diameter part of the observing optical system.

Figure 7:
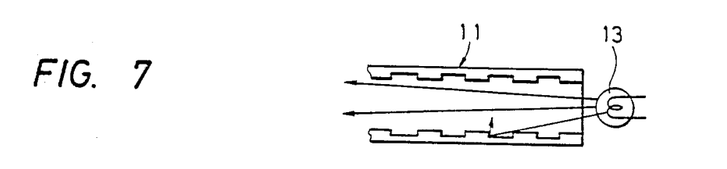
Figure 8:
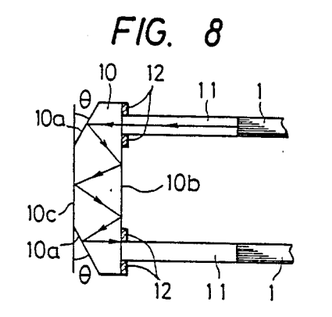
Figure 9:
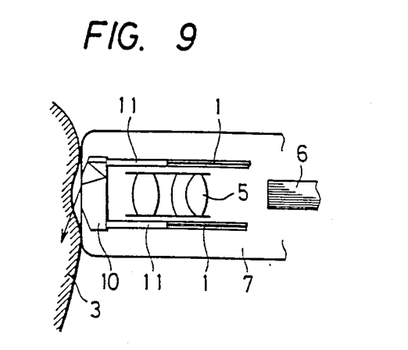

The operation of the above mentioned embodiment shall be explained in the following. In case the light transmitted through the light guide fibers 1 from a light source device not illustrated is led into the prism 10 through the transparent members 11, as shown clearly in FIG. 6, the light hitting the peripheral surface of the transparent member 11 will be absorbed by the light shielding member 11a and will not be able to pass through and therefore the divergent angle $\phi$ of the light bundle coming out by being scramble-reflected or straight proceeding through the transparent member 11 will be able to be kept comparatively small. Therefore, if such transparent member 11 is used, as shown in FIG. 7, such light source 13 as an electric bulb or strobo light will be able to be arranged directly in front of the end face of the transparent member 11. Further, as evident from this explanation, such hollow metal pipe having a diffusing surface inside as, for example, a hollow pipe threaded on the inner peripheral surface may be used instead of the transparent member 11. The light bundle having thus passed through the transparent member 11 will enter the objective side surface 10b of the prism 10 and will be reflected by the reflecting surface 10a. Here, as the angle $\theta$ (See FIG. 8) of inclination of the reflecting surface 10a to the objective side surface 10b is so selected as to totally reflect the light reflected by the reflecting surface 10a when it enters the objective side surface, as shown in FIG. 8, the light reflected by the reflecting surface 10a will be totally reflected by the objective side surface 10b, will then be totally reflected by the object side surface 10c and will then be again totally reflected by the objective side surface 10b. In such case, the entrance angles of the light with the objective side surface 10b and object side surface 10c will be kept constant. The light having thus reached the reflecting surface 10a on the side opposite the side at which it entered will be projected out of the objective side surface 10b at the same angle as the entrance angle into the prism 10 but will not be projected into the visual field of the objective 5 and will be projected out of the part of the light shielding member 12 of the objective side surface 10b as a result and will be absorbed here in fact. Now, in this state, no flare will enter the objective 5 but the object will not be able to be illuminated. However, generally the endoscope of a high magnification is used mostly with the tip part pressed against the object so that the image will not be out of focus when observed. In such using method, the light proceeding by being totally reflected through the prism 10 as described above can be projected on the object side. That is to say, as shown in FIG. 9, when the tip of the endoscope is pressed against the surface 3 of the object to be observed, water within the human body will be enclosed between the object side surface 10c of the prism 10 and the object but, as water is higher in the refractive index than air, in this state, the light proceeding through the prism 10 will be projected on the object side without being totally reflected by the object side surface 10c and will become an illuminating light to illuminate the object surface. In such case, a flennel-reflected light produced on the object side surface 10c will be totally reflected on the objective side surface 10b, therefore no light will be projected out of the objective side surface 10b and therefore no flare will enter the objective 5. The light thus projected out of the object side surface 10c will be totally reflected in case air is on the object side and will be projected on the object side with a large projecting angle. This means that the object surface will be diagonally illuminated. Therefore, the shadow of the object to be observed will be exaggerated and, as a result, a stereoscopic image will be able to be obtained. This is a peculiar effect which will not be obtained in case the object surface is illuminated in a substantially vertical direction as in the ordinary endoscope illuminating system. In the above explanation, the case that the medium on the object side is water and that on the objective side is air has been described. However, in order that the flare may be totally reflected on the objective side surface 10b of the prism 10, the relation that the refractive index $n_2$ of the material forming the prism should be larger than the refractive index $n_3$ of the medium on the objective side, that is, $n_2 > n_3$ must be satisfied. Also, in order that the illuminating light may be projected out of the object side surface 10c to the prism 10, the relation that the refractive index $n_1$ of the medium on the object side should be larger than the refractive index $n_3$ of the medium on the object side, that is, $n_1 > n_3$ must be satisfied. This shall be more particularly explained with reference to FIG. 10. Now, in case the entrance angle of the light a into the objective side surface 10b is denoted by $\alpha$, the entrance angle of the light b into the same surface is denoted by $\beta$, the entrance angle of the light c into the same surface is denoted by $\gamma$ and the critical angle on the objective side surface 10b is denoted by $\theta_1$, $\alpha < \theta_1 = \sin^{-1}(n_3/n_2)$. Therefore, the light a will be refracted by the objective side surface 10b and will pass to the side of the objective 5. Next, when the critical angle on the object side surface 10c is denoted by $\theta_2$, if the entrance angle $\beta$ satisfies the relation that $\theta_2 > \beta > \theta_1$, the light b will be totally reflected in the objective side surface 10b and will be refracted on the object side surface 10c, a part of it will proceed as a light $b_1$ into the water enclosed between the surface 3 of the object to be observed and the object side surface 10c of the prism and the other part will be flennel-reflected on the object side surface 10c, will become a light $b_2$ and will again enter the objective side surface 10b. Further, if the entrance angle $\gamma$ satisfies the relation that $\gamma > \theta_2$, the light c will proceed while being totally reflected on both of the objective side surface 10b and object side surface 10c and, as already explained, will be finally reflected by the reflecting surface 10a on the opposite side and will pass to the side of the objective 5. Now, the roles of the lights a, b and c shall be considered. First of all, the light a will pass to the side of the objective 5 through the objective side surface 10b and will become a flare. This is not preferable. Therefore, the angle $\theta$ of inclination of the prism 10 and the angle of opening of the projected light out of the transparent member 11 must be so selected that there may be no light a. The angle of opening of the projected light out of the transparent member 11 can be easily controlled by varying the length and width (thickness) of the transparent member 11. Next, the light b will be divided into two lights $b_1$ and $b_2$ by the object side surface 10c. The light $b_1$ is a light effective to cause a stereoscopic image by diagonally illuminating the surface 3 of the object to be observed. The light $b_2$ will not become a flare and therefore will have no problem. Further, the light c will not come out to the object side and therefore will not be able to be used as an illuminating light but will not be a flare. As clear from this explanation, the present invention is to utilize the light b. Therefore, the shape of the prism (transparent body) 10, the length and width (thickness) of the transparent member 11 and the angle $\epsilon$ of fitting the transparent member 11 to the prism are so selected that the entrance angle $\delta_2$ of the light fed from the light source (including the exit end face of the light guide fibers 1, the bulb 13 and strobo light) to the objective side surface 10b may be $\theta_1 < \delta_2 < \theta_2$. In this sense, it is needless to say that the objective side surface of the prism 10 need not always be such surface as has been explained above but may form a part of a spherical surface.

Figure 10:
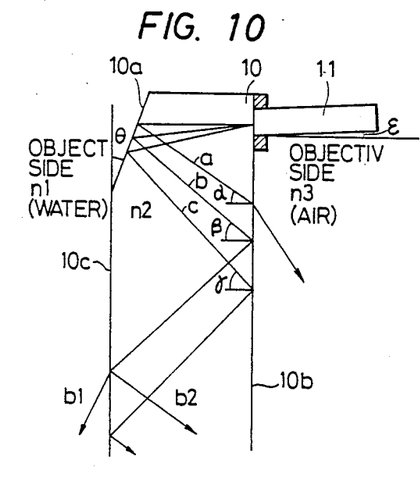
Figure 11:
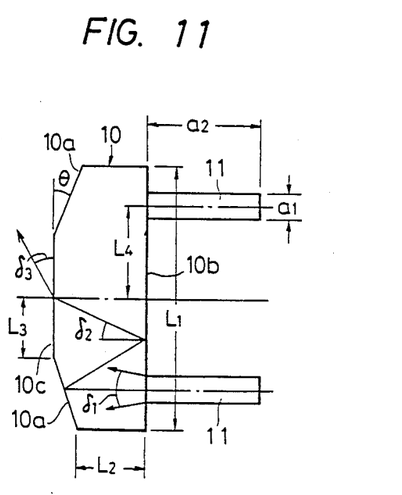

Next, the concrete dimensions of the component elements of the present illuminating optical system shall be exemplified with reference to FIGS. 10 and 11.

| $n_1 = 1.33$ | $\theta_1 = 33.7°$ |
|---|---|
| $n_2 = 1.80$ | $\theta_2 = 47.6°$ |
| $n_3 = 1.00$ | |

The dimensions of the transparent member:
$a_1 = 0.3$ mm.; $a_2 = 2.1$ mm.
Refractive index: 1.52.
The angle of fitting the transparent member 11 to the prism: $\epsilon = 0°$.
The angle of divergence of the light bundle out of the transparent member 11 in air: $\phi = 24.8°$.
The angle of divergence of the light bundle out of the transparent member 11 within the prism 10: $\delta_1 = 13.6°$.
The angle when the light reflected by the reflecting surface 10a of the prism 10 enters the objective side surface 10b:
   $\delta_2 = 37.2°$ (minimum) to 50.8° (maximum).
The angle when the light is projected into water on the objective side surface 10c of the prism 10:

$\delta_3 = 43.7°$ (minimum) to $90.0°$ (maximum).

The dimensions of the prism 10:
$l_1 = 3.0$ mm.; $l_2 = 0.6$ mm.; $l_3 = 0.8$ mm.; $\theta = 22°$ The position of fitting the transparent member 11 to the prism:

$l_4 = 1.2$ mm. (This dimension had better be so selected that the position in which the light is reflected by the objective side surface 10c may be near the optical axis of the objective 5.)

Figure 12:
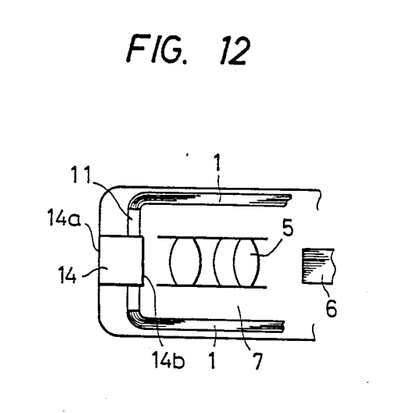
FIGS. 12 to 14 are explanatory views each for explaining the formation and operation of a tip part of a high magnification endoscope containing another embodiment of the illuminating optical system according to the present invention.
Figure 13:
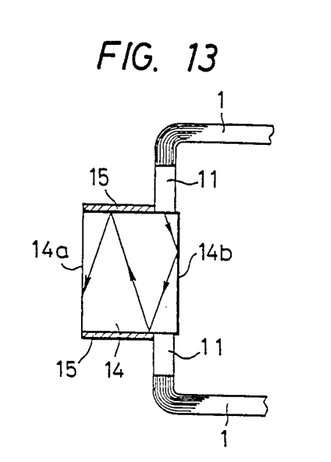
Figure 14:
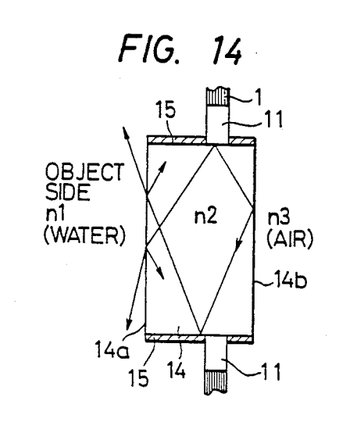

In the above, the present invention has been described in detail on the basis of typical embodiments but, in the following, various other embodiments shall be explained. First of all, in FIG. 12 is shown an embodiment wherein a rectangular parallelepipedal transparent body (prism) 14 is arranged in front of the objective 5 and transparent members 11 are connected to the tips of the light guide fibers 1 and are kept in close contact with the side surfaces of the prism 14. In such case, as shown in FIGS. 13 and 14, the side surfaces of the prism 14 are made reflecting surfaces 15 except the fitting portions for the transparent members 11 so that, when water is deposited on the object side surface 14a, the light will be projected on the object side. The flennel-reflected light produced on the object side surface 14a will be reflected on the reflecting surfaces 15, will be totally reflected on the objective side surface 14b and will be again projected out of the object side surface 14a. This process will be repeated infinite times while attenuating the intensity of the light. In such sense, this embodiment can be said to be of a system high in the efficiency of utilizing the illuminating light.

Figure 15:
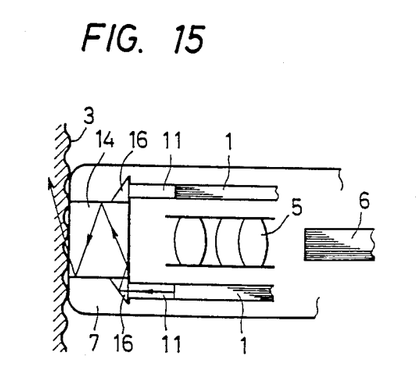
FIGS. 15 to 18 are explanatory views each showing the formation of a tip part of a high magnification endoscope containing another further embodiment of the illuminating optical system according to the present invention.

In FIG. 15 is shown an embodiment wherein the light bundles projected out of the light guide fibers 1 will be squeezed in the angle of divergence by the transparent members 11 and will be refracted by the transparent body (prism) 16 to enter the prism 14. That is to say, in this embodiment, it can be realized to introduce the light bundle into the prism 14 more easily than in the embodiment of FIG. 12 wherein the light bundles from the transparent members 11 are made to be introduced directly from the side surfaces of the prism 14.

Figure 16:
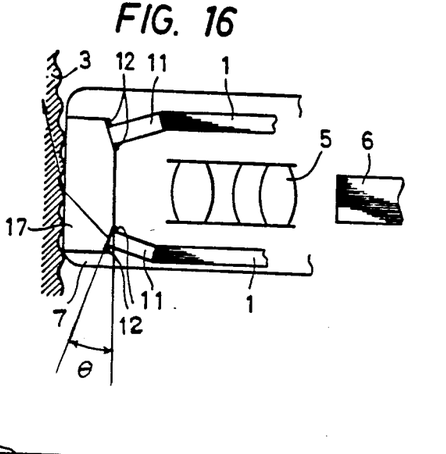

In FIG. 16 is shown an embodiment wherein the shape of the prism 17, the length and width of the transparent member 11 and the angle of fitting the transparent member 11 to the prism are so selected that, in case air is on the object side, the light bundles led into the transparent body (prism) 17 from the transparent members 11 will be totally reflected on the object side surface and will be absorbed by the light shielding members 12. In this embodiment, in case water is on the object side, the lights led into the prism 17 from the transparent members 11 will be projected on the object side from the object side surface. The flennel-reflected light produced in this case will be absorbed by the light shielding members 12 and therefore no flare will be present. That is to say, this embodiment is of a system wherein the illuminating light is projected directly out of the object side surface whereas, in the typical embodiments explained in FIGS. 4 to 11, the illuminating light is reflected by the reflecting surface 10a, is once reflected by the objective side surface 10b and is then projected out of the object side surface 10c.

Figure 17:
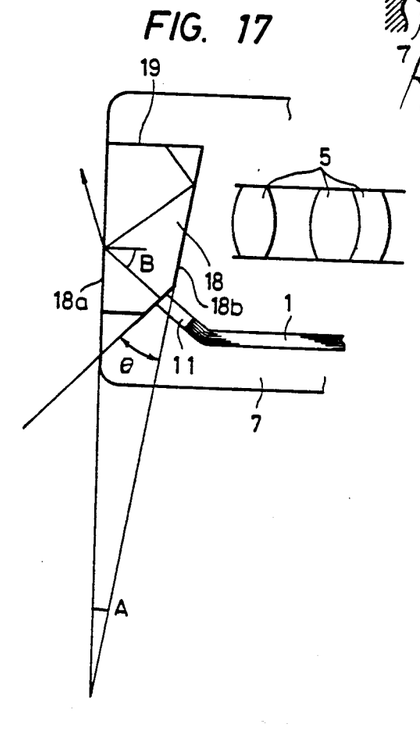

In FIG. 17 is shown an embodiment wherein the object side surface 18a and objective side surface 18b of the transparent body (prism) 18 are not in parallel with each other. In this embodiment, the angle of divergence of the light bundle projected out of the transparent member 11, the angle of the transparent member 11 with the objective side surface 18b and the angle A of the object side surface 18a with the objective side surface 18b are so selected that the light bundle from the light guide fibers 1 will be squeezed by the transparent member 11, will be projected into the prism 18, will be totally reflected or flennel-reflected by the object side surface 18a and will be always totally reflected by the objective side surface 18b. A light absorbing surface 19 is formed on the prism 18 so that the light totally reflected by the objective side surface 18b may be absorbed by this absorbing surface 19. In this embodiment, even if water is deposited on the object side surface 18a, the light will be able to be projected out of the object side surface 18a. That is to say, there are advantages that, in case the entrance angle B of the light projected into the prism 18 from the transparent member 11 into the object side surface 18a is within the range from the critical angle $\theta_3$ in air to the angle smaller by the angle A than the same critical angle $\theta_3$, the light will be able to be utilized as an illuminating light even in air and the flennel-reflected light will be totally reflected on the objective side surface 18b and will not be a flare. In other words, when $B > \theta_3$, in air, no light will be projected out of the object side surface 18a and, when $\theta_3 > B > \theta_3 - A$, in both air and water, the light will be projected but, in either case, no flare will be present.

As described above, according to the present invention, the endoscope can be used with the tip in close contact with the object to be observed, even though the magnification is high, the image will not be out of focus, as the illuminating light is projected diagonally to the surface of the object to be observed, not only the object image can be observed stereoscopically but also the illuminating light will not enter the objective side as a flare, further the amount of the light to illuminate the outside of the visual field is so small that a bright clear image can be always obtained and, in the case of photographing, a photograph very easy to see can be obtained. Further, as the same cover glass can be used for the illuminating system and observing system, not only the entire visual field can be illuminated uniformly but also the endoscope tip part can be formed to be small and compact.

Figure 18:
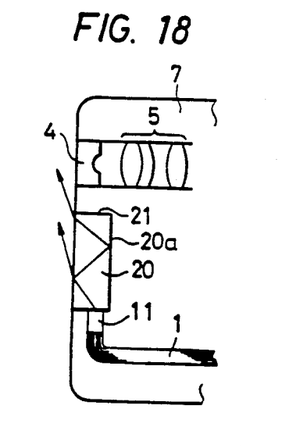

Further, in FIG. 18 is shown an embodiment wherein an illuminating optical system using the illuminating principle according to the present invention is arranged in a place different from that of the observing optical system. That is to say, according to this embodiment, the rectangular parallelepipedal prism 20 is provided parallelly with the observing optical system including the cover glass 4 and objective 5 so that the light bundle from the light source may be introduced through the already described light guide fibers 1 and tubular transparent member 11 from one side surface of the rectangular parallelepipedal prism 20. In the prism 20, the light totally reflected by the objective side surface 20a will be absorbed by the light absorbing surface 21. According to this embodiment, there is an advantage that, as the object to be observed can be diagonally illuminated, a stereoscopic object image can be obtained.

I claim:

1. An illuminating optical system for endoscopes comprising a light source and a transparent body arranged in front of said light source; the refractive indices of said transparent body and a medium located on the side near said light source from said transparent body and contacting said transparent body being so selected that, when the refractive index of said transparent body is represented by $n_2$ and the refractive index of said medium is represented by $n_3$, the condition $n_2 > n_3$ is satisfied; and the shape of said transparent body being so selected that the entrance angle of the light entering the surface of said transparent body directed to the side of said light source among lights entering said transparent body from said light source is larger than a critical angle $$\theta_1 \left( \theta_1 = \sin^{-1} \frac{n_3}{n_2} \right)$$

at the entering point of the light, and wherein said transparent body is a rectangular parallelepipedal prism having a first surface intersecting at right angles with the optical axis of an objective set in the rear of said transparent body adjacently to said transparent body and facing said objective, a second surface located forward of said first surface and parallel with said first surface and four side surfaces parallel with said optical axis and said illuminating optical system further comprises at least one tubular transparent member adjacent on one end face to said light source and contacting on the other end face with said side surface to lead the light from said light source into said prism.

2. An illuminating optical system according to claim 1 wherein a light shielding member is provided on said first surface except in the effective diameter part of said objective and said side surfaces are made reflecting surfaces except in the connecting parts with said tubular transparent members.

3. An illuminating optical system according to claim 1 or 2 wherein a plurality of said tubular transparent members are arranged around said objective.

4. An illuminating optical system according to claim 1 or 2 wherein said tubular transparent member has an outer peripheral surface provided thereon with a light shielding member and an inner peripheral surface which can scramble-reflect the light introduced into the interior.

5. An illuminating optical system according to claim 1 or 2 wherein said tubular transparent member is a metal pipe having a threaded inner peripheral surface.

6. An illuminating optical system for endoscopes comprising a light source and a transparent body arranged in front of said light source; the refractive indices of said transparent body and a medium located on the side near said light source from said transparent body and contacting said transparent body being so selected that, when the refractive index of said transparent body is represented by $n_2$ and the refractive index of said medium is represented by $n_3$, the condition $n_2 > n_3$ is satisfied; and the shape of said transparent body being so selected that the entrance angle of the light entering the surface of said transparent body directed to the side of said light source among lights entering said transparent body from said light source is larger than a critical angle $$\theta_1 \left( \theta_1 = \sin^{-1} \frac{n_3}{n_2} \right)$$

at the entering point of the light, and wherein said transparent body is a rectangular parallelepipedal prism having a first surface intersecting at right angles with the optical axis of an objective set in the rear of said transparent body adjacently to said transparent body and facing said objective, a second surface located forward of said first surface and parallel with said first surface and four side surfaces parallel with said optical axis and said illuminating optical system further comprises at least one tubular transparent member adjacent on one end surface to said light source and a triangular prism having a first surface contacted with the other end face of said tubular transparent member and a second surface intersecting at right angles with said first surface and contacted with the side surface of said rectangular parallelepipedal prism to lead the light from said light into said rectangular parallelepipedal prism.

7. An illuminating optical system according to claim 6 wherein a light shielding member is provided on said first surface except in the effective diameter part of said objective and said side surfaces are made reflecting surfaces except in the connecting part with said triangular prism.

8. An illuminating optical system according to claim 6 or 7 wherein a plurality of sets of said tubular transparent members and triangular prisms are arranged around said objective.

9. An illuminating optical system according to claim 6 or 7 wherein said tubular transparent member has an outer peripheral surface provided thereon with a light shielding member and an inner peripheral surface which can scramble-reflect the light introduced into the interior.

10. An illuminating optical system according to claim 6 or 7 wherein said tubular transparent member is a metal pipe having a threaded inner peripheral surface.

11. An illuminating optical system for endoscopes comprising a light source and a transparent body arranged in front of said light source; the refractive indices of said transparent body and a medium located on the side near said light source from said transparent body and contacting said transparent body being so selected that, when the refractive index of said transparent body is represented by $n_2$ and the refractive index of said medium is represented by $n_3$, the condition $n_2 > n_3$ is satisfied; and the shape of said transparent body being so selected that the entrance angle of the light entering the surface of said transparent body directed to the side of said light source among lights entering said transparent body from said light source is larger than a critical angle $$\theta_1 \left( \theta_1 = \sin^{-1} \frac{n_3}{n_2} \right)$$

at the entering point of the light, and wherein said transparent body is a prism having a first surface intersecting at right angles with the optical axis of an objective set in the rear of said transparent body adjacently to said transparent body and facing said objective, a second surface located forward of said first surface and parallel with said first surface and a third surface contacting at an angle $\theta$ with said first surface and said illuminating optical system further comprises at least one tubular transparent member adjacent on one end face to said light source and contacting on the other end face with said third surface to lead the light from said light source into said prism.

12. An illuminating optical system according to claim 11 wherein a light shielding member is provided on said first and third surfaces except in the effective diameter part of said objective and the connecting part with said tubular transparent member.

13. An illuminating optical system according to claim 11 or 12 wherein a plurality of said tubular transparent members are arranged around said objective.

14. An illuminating optical system according to claim 11 or 12 wherein said tubular transparent member has an outer peripheral surface provided thereon with a light shielding member and an inner peripheral surface which can scramble-reflect the light introduced into the interior.

15. An illuminating optical system according to claim 11 or 12 wherein said tubular transparent member is a metal pipe having a threaded inner peripheral surface.

16. An illuminating optical system according to claim 11 wherein said angle $\theta$ is so selected that, in case air is in contact with said second surface, the light led into said prism is totally reflected on said second surface.

17. An illuminating optical system for endoscopes comprising a light source and a transparent body arranged in front of said light source; the refractive indices of said transparent body and a medium located on the side near said light source from said transparent body and contacting said transparent body being so selected that, when the refractive index of said transparent body is represented by $n_2$ and the refractive index of said medium is represented by $n_3$, the condition $n_2 > n_3$ is satisfied; and the shape of said transparent body being so selected that the entrance angle of the light entering the surface of said transparent body directed to the side of said light source among lights entering said transparent body from said light source is larger than a critical angle $$\theta_1 \left( \theta_1 = \sin^{-1} \frac{n_3}{n_2} \right)$$

at the entering point of the light, and wherein said transparent body is a prism having a first surface forming a predetermined angle $(A+90°)$ with the optical axis of an objective set in the rear of said transparent body adjacently to said transparent body and facing said objective, a second surface located forward of said first surface and intersecting at right angles with said optical axis and a third surface contacting at an angle $\theta$ with said first surface and said illuminating optical system further comprises a tubular transparent member adjacent on one end face to said light source and contacting on the other end face with said third surface to lead the light from said light source into said prism.

18. An illuminating optical system according to claim 17 wherein a light shielding member is provided on said first and third surfaces except in the effective diameter part of said objective and the connecting part with said tubular transparent member and the outer peripheral surface of said prism is formed as a light absorbing surface.

19. An illuminating optical system according to claim 17 or 18 wherein said tubular transparent member has an outer peripheral surface provided thereon with a light shielding member and an inner peripheral surface which can scramble-reflect the light introduced into the interior.

20. An illuminationg optical system according to claim 17 or 18 wherein said tubular transparent member is a metal pipe having a threaded inner peripheral surface.

21. An illuminating optical system according to claim 17 wherein said angles A and $\theta$ are so selected that the light led into said prism is totally reflected on said second surface and the lights totally reflected and flennel-reflected on said third surface are totally reflected on said first surface.

22. An illuminating optical system as in claim 17 wherein said angle $\theta$, said angle A where $A \geq 0$, said refractive index $n_2$, said refractive index $n_3$, and the refractive index of a medium located on an object side surface of said transparent body are so selected that the entrance angle of the light entering said first surface directed to the side of said light source by reflecting on said second surface among lights emitted from said light source is larger than a critical angle $$\theta_1 \left( \theta_1 = \sin^{-1} \frac{n_3}{n_2} \right).$$

23. An illuminating optical system for endoscopes according to claim 17, wherein said tubular transparent member has an innter peripheral surface absorbing or scramble-reflecting the light to set the entrance angle of the light onto said first surface together with the length and thickness of said tubular transparent member.

24. An illuminating optical system as in claim 17 wherein said angle A is zero and $n_1 \geq n_3$ is satisfied, $n_1$ being said refractive index of a medium located on an object side surface of said transparent body.

25. An illuminating optical system for endoscopes according to claim 24, wherein said tubular transparent member has an inner peripheral surface absorbing or scramble-reflecting the light to set the entrance angle of the light onto said first surface together with the length and thickness of said tubular transparent member.

26. An illuminating optical system for endoscopes comprising a light source and a transparent body arranged in front of said light source; the refractive indices of said transparent body and a medium located on the side near said light source from said transparent body and contacting said transparent body being so selected that, when the refractive index of said transparent body is represented by $n_2$ and the refractive index of said medium is represented by $n_3$, the condition that $n_2 > n_3$ is satisfied; and wherein said transparent body is a prism having a first surface forming a predetermined angle $(A+90°)$ with the optical axis of an objective set in the rear of said transparent body adjacently to said transparent body and facing said objective, a second surface located forward of said first surface and interesecting at right angles with said optical axis and a third surface contacting at an angle $\theta$ with said first surface and said illuminating optical system further comprising a tubular transparent member adjacent on one end face to said light source and contacting on the other end face with said third surface to lead the light from said light source into said prism, and wherein said angle $\theta$, said refractive index $n_2$, said refractive index $n_3$, and said angle A are so selected that the entrance angle of the light entering said first surface directed to the side of said light source by reflecting on said second surface among lights emitted from said light source is larger than a critical angle $$\theta_1 \left( \theta_1 = \sin^{-1} \frac{n_3}{n_2} \right)$$

in consideration of the refractive index of a medium located on the object side surface of said transparent body.

* * * * *